United States Patent [19]

Scott

[11] Patent Number: 4,589,477

[45] Date of Patent: May 20, 1986

[54] SAMPLE CELL TEMPERATURE STABILIZER

[75] Inventor: Raymond P. W. Scott, Wilton, Conn.

[73] Assignee: The Perkin-Elmer Corporation, Norwalk, Conn.

[21] Appl. No.: 576,660

[22] Filed: Feb. 3, 1984

[51] Int. Cl.$^4$ .............................................. F25B 29/00
[52] U.S. Cl. ........................................ 165/66; 422/70; 422/161; 165/61
[58] Field of Search .................. 165/61, 66; 422/70, 422/161; 73/61.1 C

[56] References Cited

U.S. PATENT DOCUMENTS

| 3,799,250 | 3/1974 | Dyre ....................................... 165/61 |
| 4,233,030 | 11/1980 | Twitchett et al. ................ 422/70 X |
| 4,248,259 | 2/1981 | Kaartinen et al. ....................... 62/66 |
| 4,403,147 | 9/1983 | Melera et al. ................ 73/61.1 C X |

FOREIGN PATENT DOCUMENTS 5679 6/1972 Japan .............................. 73/61.1 C Primary Examiner—Albert W. Davis, Jr.
Assistant Examiner—Peggy A. Neils
Attorney, Agent, or Firm—F. L. Masselle; E. T. Grimes

[57] ABSTRACT

An apparatus for equilibrating the temperature of the eluate of a separating column entering a flow cell includes the provision of a heat transfer relationship between the outlet fluid and the inlet conduit whereby the temperature of the fluid, as it passes through the flow cell, is stabilized.

3 Claims, 1 Drawing Figure

SAMPLE CELL TEMPERATURE STABILIZER

BACKGROUND OF THE INVENTION

The present invention generally relates to a flow cell apparatus and, in particular, relates to such an apparatus for equilibrating the temperature of a fluid passing therethrough.

Sample cells are available in a variety of shapes, sizes and configurations. In addition, heat exchangers for use therewith are also known. The primary purpose of previous heat exchangers is to merely remove thermal energy from the sample cell. Very often such a heat exchanger functions by transferring thermal energy to a moving working fluid, which can, of course, be a gas, and which, subsequently, carries the transferred thermal energy away from its source.

However, in many applications, the simple removal of thermal energy is not quite as important as is the ability to equilibrate, or stabilize, the temperature of a flowing fluid on both sides of a device through which the fluid is passed.

One device where such equilibration is highly desirable is the flow cell of a liquid chromatography system. In a liquid chromatography system, the eluate of the separating column exits at a rather elevated temperature and is conveyed, via a relatively short connecting conduit, to a measuring flow cell. Often, a measuring light beam is passed through the flow cell and the intensity reduction of the light beam during its passage through the cell is a measure of the absorbance of the fluid passing therethrough. Frequently, if the temperature of the eluate of the separating column is significantly different from the flow cell, even if such a temperature difference may be an acceptable consequence of a particular separation, unacceptable noise may nevertheless result in the detection mechanism of the chromatograph. Hence, it is often desirable to stabilize the temperature of an eluate from a separating column. However, if such a temperature stabilization is performed it is quite important to maintain that temperature at a constant level.

Conventionally, this result is accomplished by employing known heat exchanging mechanisms. For example, by providing a water jacket about the sample cell and/or the inlet conduit. The desired temperature is then obtained by circulating a coolant through the jacket at a selected flow rate. Such an arrangement requires careful monitoring and controlling of both the coolant temperature and the flow rate. The provision of such monitoring and controlling usually requires considerable expenditures and often complex mechanisms.

SUMMARY OF THE INVENTION

Accordingly, it is one object of the present invention to provide an apparatus for equilibriating the temperature of a fluid passing through a flow cell.

This object is accomplished, at least in part, by providing a flow cell and thermal communication between the inlet conduit and the outlet fluid thereof.

Other objects and advantages will become apparent to those skilled in the art from the following detailed description read in conjunction with the appended claims and the drawing attached hereto.

BRIEF DESCRIPTION OF THE DRAWING

The single FIGURE of the drawing, not drawn to scale is a pictorial view, partially in section, of a flow cell apparatus embodying the principles of the present invention.

DETAILED DESCRIPTION OF THE INVENTION

Figure 1:
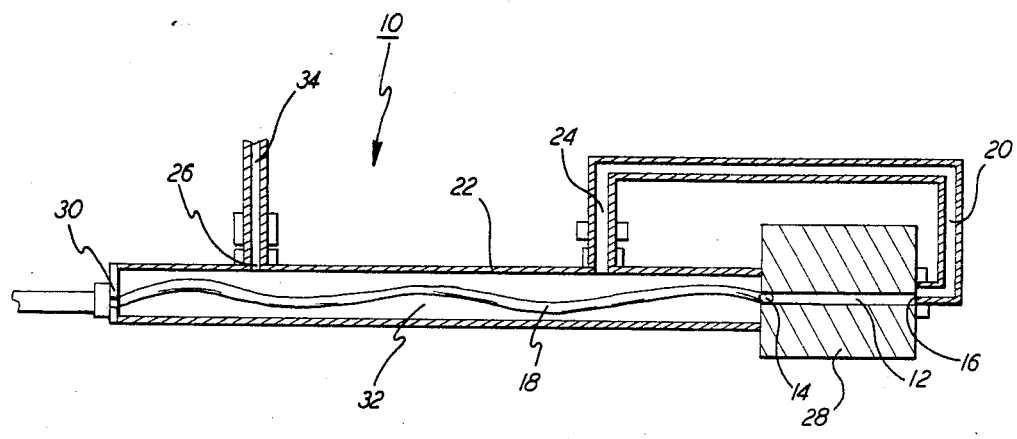

An apparatus, generally indicated at 10 in the drawings and embodying the principles of the present invention includes a flow cell 12 having an inlet port 14 and an outlet port 16. The apparatus 10 further includes a thermally conductive inlet conduit 18 in fluid communication with the inlet port 14 and an outlet conduit 20 in fluid communication with the outlet port 16. The apparatus 10 also includes an encasement sheath 22 about the inlet conduit 18. The encasement sheath 22 includes an input port 24 proximate the flow cell 12 and an output port 26, spaced apart and distal the input port 24. The outlet port 16 of the flow cell 12 is in fluid communication with the input port 24 of the sheath 22 via the outlet conduit 20.

Preferably, the flow cell 12 is within a thermally conductive flow cell housing 28. The effective liquid volume of the flow cell 12 is selected according to well known chromatographic criteria.

In one preferred embodiment, the eluate of a chromatographic separation column, not shown, is directed to a sheath input fitting 30. The fitting 30 directly communicates the eluate exiting the outlet conduit 20 about the inlet conduit 18 which is within the sheath 22. The inlet conduit 18 preferably has an inside diameter of about 0.025 cm and an outside diameter of about 0.050 cm. In one arrangement where the inlet conduit 18 is straight the length thereof is minimized to minimize the band dispersion of the eluate. However, if the inlet conduit 18 is a two-dimensional serpentine a considerably greater length can be used without adversely increasing the band dispersion. As used herein the term "serpentine" is taken to mean a continuously curving path having periodic peaks and valleys of substantially uniform amplitude. As a consequence of the serpentine path, it is understood that the radial velocity of a fluid passing through the serpentine path is continuously changing in magnitude as well as periodically reversing direction. One such "serpentine" conduit is described in U.S. patent application Ser. No. 471,910 filed on Mar. 3, 1983 and assigned to the assignee hereof. The teaching of which is hereby incorporated herein. As more fully discussed below, the use of a serpentine inlet conduit 18 enhances the thermal equilibration of the flow cell 12.

The outlet conduit 20 directs the fluid exiting the flow cell 12 to the interior 32 of the sheath 22. Hence, the thermally conductive inlet conduit 18 is in a thermal exchange relationship with the exiting fluid over substantially it's entire length. However, to ensure maximum fluid circulation about the inlet conduit 18 the input port 24 of the sheath 22 should be as close to the housing 28 as is practical. Further, the output port 26 of the sheath 22 should be as close to the column end of the sheath 22 as is possible. In practice, the fluid exiting the sheath 22 via the output port 26 thereof is usually directed to a waste vessel, not shown, via a waste fluid conduit 34.

In the preferred embodiment, the inlet conduit 18 is serpentine having a linear distance between adjacent peaks of about 0.1 cm, peak to peak amplitude of about 0.05 cm and a sheathed length of about 20 cm. The inlet conduit 18 is stainless steel. The outlet conduit 20 has an inside diameter of about 0.05 cm and an outside diameter of about 0.075 cm. The inside diameter of the outlet conduit 20 is essentially irrelevant since maintanence of the separated bands in the eluate is insignificant after passage through the flow cell 12. In this embodiment, the sheath 22 is a stainless steel tube having an inside diameter of about 0.1 cm and an outside diameter of about 0.17 cm.

As known, there is a temperature difference between the fluid entering the flow cell 12 and the fluid exiting therefrom. In the embodiment discussed above, this temperature drop is primarily due to the heat dissipation via the flow cell housing 28. Further, it is clear that the thermal equilibrating effect of the flow cell housing 28 is minimal. However, in the present apparatus 10, since the outlet fluid operates as the working fluid in a heat exchanger, a steady state heat transfer is established between the inlet conduit 18 and the outlet fluid.

From the above, it is recognized that the use of the outlet fluid in such a fashion over the sheathed length of the inlet conduit 18 stabilizes the temperature of the entering fluid. Consequently, measurement inaccuracies due to perturbations in the temperature of the eluate are virtually eliminated.

The thermal equilibration is further enhanced, and more quickly stabilized, by use of a serpentine inlet conduit 18. This enhancement results due to the continuous predominant radial flow of the eluate across the internal diameter of the serpentine which increases the transfer of thermal energy through the inlet conduit 18. In addition, the simple fact of exposing more surface area to the fluid within the sheath 22 enhances the equilibration process. Consequently, a stable steady state is more rapidly reestablished after any perturbation in the temperature of the eluate.

The present invention has been decribed herein with reference to a specific exemplary embodiment. It is understood that other configurations and arrangements may be developed by those skilled in the art without departing from the principles described herein. As such, the present invention is deemed limited only by the appended claims and the reasonable interpretation thereof.

What is claimed is:

1. In a liquid chromatograph, thermal stablizing apparatus comprising, in combination:
    a flow cell with an inlet port and an outlet port;
    an inlet conduit communicating with said inlet port, said inlet conduit comprising a two dimensional continuous serpentine shaped conduit portion one end of which couples to said inlet port;
    outlet conduit communicating with said outlet port and surrounding said serpentine shaped conduit portion, the column fluid passing through said inlet conduit, said flow cell and said outlet conduit so as to stabilize the temperature of the fluid as it passes through said flow cell.

2. The apparatus of claim 1 wherein said inlet conduit has an inside diameter of about 0.025 cm and an outside diameter of about 0.05 cm.

3. The apparatus of claim 2 wherein adjacent peaks of said serpentine portion are about 0.1 cm apart with a peak to peak amplitude of 0.05 cm.

* * * * *